US012758256B2

(12) United States Patent
Kee et al.

(10) Patent No.: US 12,758,256 B2
(45) Date of Patent: Oct. 13, 2026

(54) NEEDLE LOCK DEVICE AND A NEEDLE GUIDE SYSTEM

(71) Applicant: Biobot Surgical Pte. Ltd., Singapore (SG)

(72) Inventors: Yew Hwee Kee, Singapore (SG); Jia Yun Hee, Singapore (SG); Lan Eng Poh, Singapore (SG); Guoyu Qian, Singapore (SG)

(73) Assignee: Biobot Surgical Pte. Ltd., Singapore (SG)

( * ) Notice: Subject to any disclaimer, the term of this patent is extended or adjusted under 35 U.S.C. 154(b) by 24 days.

(21) Appl. No.: 18/855,915

(22) PCT Filed: Apr. 13, 2023

(86) PCT No.: PCT/SG2023/050251
§ 371 (c)(1),
(2) Date: Oct. 10, 2024

(87) PCT Pub. No.: WO2023/200403
PCT Pub. Date: Oct. 19, 2023

(65) Prior Publication Data
US 2025/0235237 A1 Jul. 24, 2025

(30) Foreign Application Priority Data
Apr. 13, 2022 (SG) ............................ 10202203852T

(51) Int. Cl.
*A61B 17/34* (2006.01)

(52) U.S. Cl.
CPC ... *A61B 17/3403* (2013.01); *A61B 2017/3411* (2013.01); *A61B 2017/347* (2013.01)

(58) Field of Classification Search
CPC ........ A61B 17/3403; A61B 2017/3411; A61B 2017/347; A61N 2005/1012; A61N 5/1027
See application file for complete search history.

(56) References Cited

U.S. PATENT DOCUMENTS 6,036,632 A 3/2000 Whitmore, III et al.
6,508,786 B2 1/2003 Huitema et al.
(Continued)

OTHER PUBLICATIONS

International Search Report and of the ISA issued in PCT/SG2023/050251, mailed Oct. 31, 2023; ISA/SG.
(Continued)

*Primary Examiner* — Sarah A Long
(74) *Attorney, Agent, or Firm* — Harness, Dickey & Pierce, P.L.C.

(57) ABSTRACT

A needle lock device includes an outer frame, a plurality of support members mounted to the outer frame and a plurality of needle holders. At least one needle holder is disposed on each of the support members and each needle holder defining a passage configured to receive a needle. The needle lock device further includes a lock mechanism configured to operate each needle holder between a free state, wherein the needle holder is movable relative to the outer frame and allows translation of the needle through the passage, and a locked state, wherein the needle holder is fixed relative to the outer frame and prevents translation of the needle through the passage. Each needle holder may be compressible for varying a size of the passage between the free state and the lock state. Each lock member may comprise a cam profile and is rotatable between a first position and a second position for operating an adjacent needle holder between the free state and the locked state.

16 Claims, 9 Drawing Sheets

(56) References Cited

U.S. PATENT DOCUMENTS

| | | | | |
|---|---|---|---|---|
| 2002/0198518 | A1 | 12/2002 | Mikus et al. | |
| 2003/0139642 | A1* | 7/2003 | Hogendijk | A61N 5/1007 600/7 |
| 2009/0292244 | A1 | 11/2009 | Flagle et al. | |
| 2011/0105823 | A1 | 5/2011 | Single, Jr. et al. | |
| 2018/0214140 | A1 | 8/2018 | Nock et al. | |
| 2019/0231471 | A1* | 8/2019 | Glossop | A61B 90/39 |
| 2020/0000443 | A1* | 1/2020 | Noras | A61B 17/3403 |
| 2020/0077993 | A1 | 3/2020 | Yap et al. | |
| 2021/0016104 | A1* | 1/2021 | Cavanaugh | A61B 17/3403 |

OTHER PUBLICATIONS

European Search Report for European Application No. 223788703. 9-1122 / 4507600 PCT/SG2023050251, dated Jan. 27, 2026 (10 Pages).

* cited by examiner

1200

NEEDLE LOCK DEVICE AND A NEEDLE GUIDE SYSTEM

CROSS-REFERENCE TO RELATED APPLICATIONS

This application is a 371 U.S. National Stage of International Application No. PCT/SG2023/050251, filed on Apr. 13, 2023, which claims priority to Singapore Application No. 10202203852T, filed on Apr. 13, 2022. The entire disclosures of the above applications are incorporated herein by reference.

FIELD OF INVENTION

The present invention relates broadly, but not exclusively, to a needle lock device and a needle guide system.

BACKGROUND

In minimally invasive prostate treatment procedures, multiple needles are inserted transperineally into the prostate. Such procedures may include, for example, low dose rate (LDR) or high dose rate (HDR) brachytherapy, irreversible electroporation, laser ablation, or cryoablation.

Ensuring minimal displacement of needles is crucial to the safety and efficacy of the treatment. This is because needle displacement can result in inaccuracy of treatment delivery. Needle displacement may be caused by patient movement, prostate swelling, or other activities in the vicinity during the operating procedure.

Various accessories exist to guide and lock needles in place during such treatments. U.S. Pat. No. 6,036,632A describes a disposable template grid forming a plurality of passages adapted to allow the needle to pass. U.S. Pat. No. 6,508,786B2 describes a needle guide template defining an array of close-fitting through-holes to guide needles inserted therethrough; which locks the position of one or more needles inserted in the template. However, a drawback of these systems is that they constrain the needle to limited locations and trajectories. This may not be the optimal treatment configuration. For example, access to anterior and posterior lesions via an angulated trajectory is a challenge. It can also be difficult to avoid critical structures.

There have been attempts to allow more flexibility in needle trajectories, while providing some form of support. For example, US2011105823-A1 describes a medical template device for use in positioning therapeutic probes at a target tissue comprising a frame and a pierceable probe guide capable of being pierced at any location along its surface by a therapeutic probe. However, these do not address the requirement of locking needles securely in place.

Navigational platforms exist that enable not just freedom in needle placement but an accurate way of doing so. Examples include US20200077993A1 which describes an Apparatus and method for biopsy and therapy.

The need to lock needles in place, and the option of allowing freedom in needle placement, are two requirements that are inherently challenging to fulfil simultaneously.

A need therefore exists to provide a device and a system that can address at least some of the above problems.

SUMMARY

According to a first aspect of the present invention, there is provided a needle lock device comprising:

an outer frame;

a plurality of support members mounted to the outer frame;

a plurality of needle holders, wherein at least one needle holder is disposed on each of the support members, each needle holder defining a passage configured to receive a needle; and a lock mechanism configured to operate each needle holder between a free state and a locked state, wherein, in the free state, the needle holder is movable relative to the outer frame and allows translation of the needle through the passage, and wherein, in the locked state, the needle holder is fixed relative to the outer frame and prevents translation of the needle through the passage.

The needle holder may be compressible for varying a size of the passage between the free state and the lock state.

The support member may comprise at least one concave recess, and each of the at least one needle holder may be disposed in a respective concave recess.

The device may further comprise a plurality of alignment members each configured to align a longitudinal axis of the passage of a respective needle holder along a direction substantially perpendicular to a plane formed by the outer frame.

The device may further comprise retention means configured to retain each needle holder in the respective recess.

In one embodiment, the plurality of support members may be parallel to each other, and the lock mechanism may comprise a plurality of parallel lock members mounted to the outer frame such that the support members are substantially perpendicular to the lock members, the support members and lock member may define a grid for containing the needle holders.

Each lock member may comprise a cam profile and may be rotatable between a first position and a second position for operating an adjacent needle holder between the free state and the locked state.

Each lock member may be configured to rotate at an opposite direction from an adjacent lock member.

In another embodiment, each of the support members may comprise an elongated rod having ends supported by the outer frame, the elongated rod being rotatable about its longitudinal axis.

The at least one needle holder may be slidable and swivelable about the respective support member.

The lock mechanism may comprise a plurality of clasps and each clasp may be attached to a respective needle holder and configured to operate the needle holder between the free state and the locked state.

The lock mechanism may be further configured to restrict rotation of selected one or more support members.

According to a second aspect of the present invention, there is provided a needle guide system comprising:

the needle lock device according to the embodiments mentioned above;

a user interface device; and a processor;

wherein the user interface device is configured to provide a plurality of entry points corresponding to the passages of the plurality of needle holders; and wherein, based on a selected target point, the processor is configured to deter-mine an entry point satisfying one or more parameters.

The one or more parameters may comprise a shortest distance between the entry point and the target point.

The one or more parameters may comprise an absence of a critical structure between the entry point and the target point.

The one or more parameters may comprise a preset angle between the entry point and the target point.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
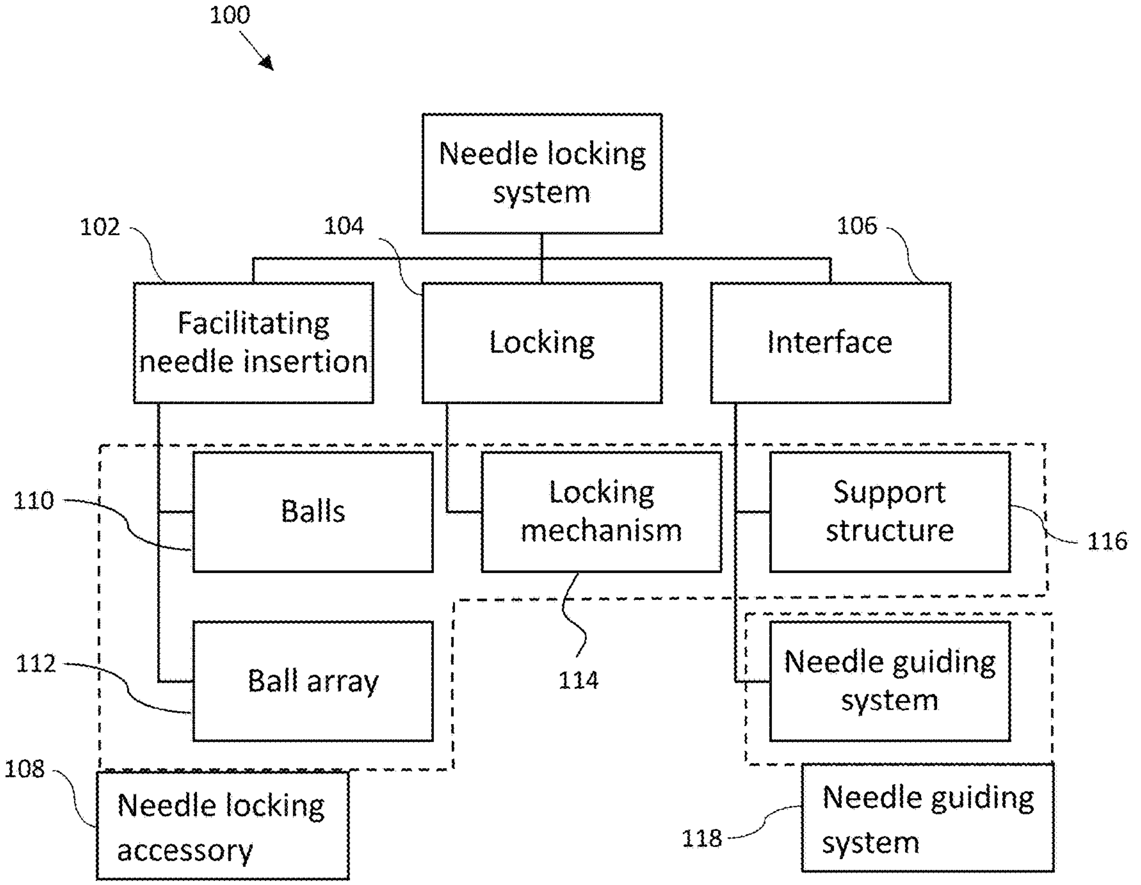
FIG. 1 shows a schematic diagram of an overview of a needle lock system, according to an embodiment.

Embodiments will be described, by way of example only, with reference to the drawings. Like reference numerals and characters in the drawings refer to like elements or equivalents.

FIG. 1 shows a schematic block diagram of a needle lock system 100, according to an embodiment. As shown in FIG. 1, the key functions of the needle lock system 100 are facilitating needle insertion as represented by box 102, locking a needle as represented by box 104, and interfacing with related elements as represented by box 106. These functions can be achieved by integrating a needle lock accessory or device 108 and a needle guide system 118. The needle lock device 108 comprises a needle holder 110 (also referred to as balls), a needle holder array 112 (also referred to as ball array), and a lock mechanism 114. A support structure 116 can provide an interface for supporting the needle lock device 108, which can receive a needle inserted by the needle guide system 118, as described in further detail below.

Figures 2A, 2B, 2C:
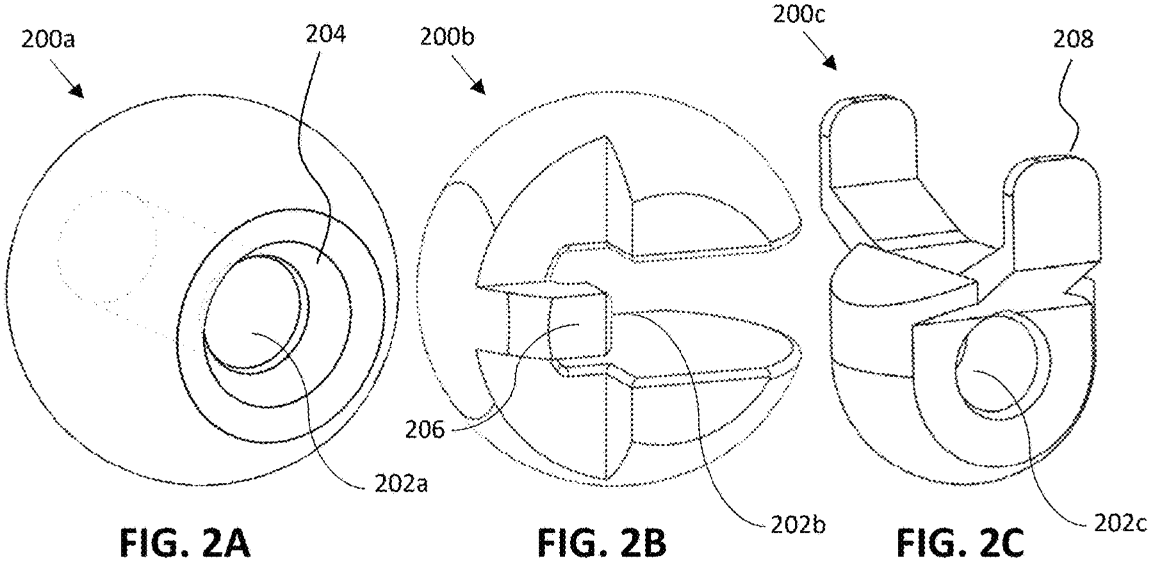
FIG. 2A shows an enlarged perspective view of a needle holder, according to an embodiment.
FIG. 2B shows an enlarged perspective view of a needle holder, according to another embodiment.
FIG. 2C shows an enlarged perspective view of a needle holder, according to another embodiment.

In embodiments of the present disclosure, the needle holder 110 serves as a channel for a needle to pass through and may contain a passage which may be adapted to the size of the needle, and which the needle may pass through. The needle holder 110 may be configured to be compressible such that a size of the passage can be varied when compressive force is applied to the needle holder 110. For example, the needle holder 110 can be made of an elastomeric material such as polyurethane. FIGS. 2A-2C shows needle holders 200*a*, 200*b*, 200*c*, which can be used as the needle holder 110 of FIG. 1, according to alternate embodiments. Each needle holder 200*a*, 200*b*, 200*c* includes a passage 202*a*, 202*b*, 202*c* respectively. In one example, the external shape of the needle holder 200*a* may be spherical, allowing the needle holder 200*a* to rotate in position to accommodate various angles of needle insertion. Additionally, there can be a funnel shaped structure 204 at an entrance of the passage 202*a* to facilitate entry of the needle as illustrated in FIG. 2A. In another example, the needle holder 200*b* can be C-shaped as illustrated in FIG. 2B. The C-shaped structure comprises a protrusion 206 which can help retain the needle holder 200*b* within the needle holder array 112.

Figure 3A:
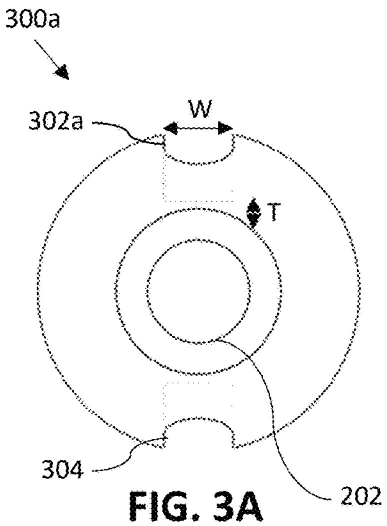
FIG. 3A shows a front view of a needle holder with slot on the top and bottom side, according to an embodiment.
Figure 3B:
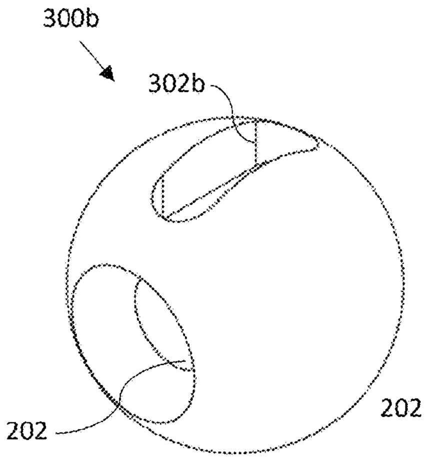
FIG. 3B shows a perspective view of a needle holder with straight slot on the top side, according to an embodiment.
Figure 3C:
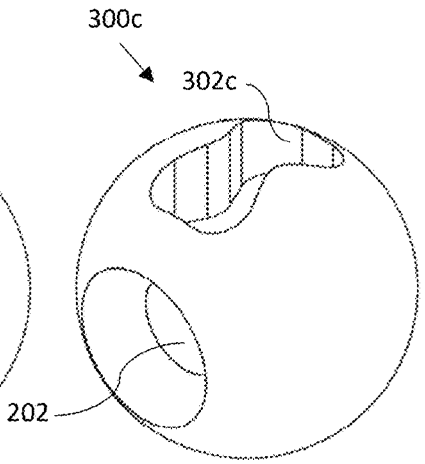
FIG. 3C shows a perspective view of a needle holder with hourglass-shaped slot on the top side, according to an embodiment.

FIG. 3A shows a front view of a needle holder 300*a* similar to the needle holder 200*a* of FIG. 2A, but with slots 302*a*, 304 formed substantially diagonally opposite each other. In this embodiment, material is removed on the top and/or bottom side of the needle holder 300*a* to form one or more slots 302*a*, 304 to reduce the force required to compress the needle holder 300*a*. The slots 302*a*, 304 help to concentrate the forces of a cam to only act in compressing the material to grip the needle. Removal of the material in the slots 302*a*, 304 helps to relieve the stress in the area that the force is not required, therefore reducing the actuation forces in the lock mechanism 114. The dimensions of the slot 302*a*, 304 can be optimized based on factors including but not limited to the required compressive force, the material of needle holder 300*a*, etc. For example, the slot 302*a*, 304 can be a through slot or a blind slot. There can be a minimum thickness (T) of up to 0.5 mm in the case of a blind slot. The slots 302*a*, 304 can have a width (W) of 0.2 to 1 mm. The slot 302*a*, 304 may be in a variety of shapes, for example, a straight slot 302*b* as illustrated in FIG. 3B or an hourglass shaped slot 302*c* as illustrated in FIG. 3C.

Figure 4:
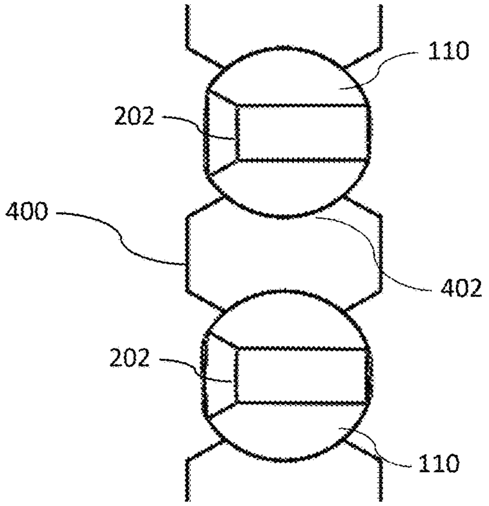
FIG. 4 shows a cross-section view of needle holders disposed onto recesses of supporting members, according to an embodiment.
Figure 5A:
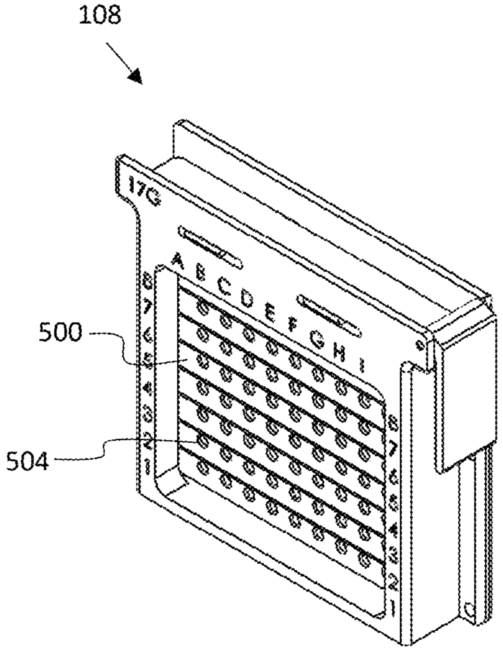
FIG. 5A shows a perspective view of a needle lock device with front and back frames, according to an embodiment.
Figure 5B:
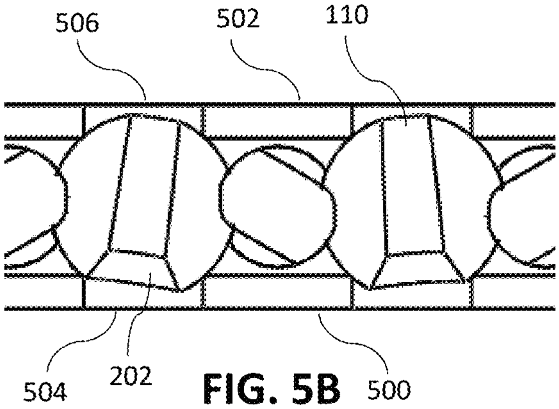
FIG. 5B shows a cross-section view of needle holders mounted in between a front frame and a back frame in the needle lock device of FIG. 5A.

In some embodiments, the needle holders 110 can be arranged in a regular needle holder array 112, aligned in columns and rows (similar to a grid). To restrain the needle holders 110 in the grid-like configuration, the needle holders 110 are supported by support members 400 (FIG. 4) which may be in the form of a plurality of plates. For example, a series of parallel plates can be stacked to form the grid layout. These support members 400 can support the needle holders 110 above and below, in the front and back, at the lateral sides, or a combination of the above. Additionally, each needle holder 110 may be contained within a respective recess 402 on the support members 400, hence the needle holder's 110 position on the grid is maintained. As illustrated in FIG. 4, the recess 402 can be concave and can conform to the shape of the needle holder 110, therefore allowing free rotation of the needle holder 110. The recess 402 may be deep enough such that they prevent the needle holder 110 from being squeezed out. Alternatively or in addition, the support members can have walls at the front and back. As illustrated in FIGS. 5A and 5B, the walls 500, 502 may comprise holes 504, 506 where the needle may enter and exit the passage 202 of the needle holder 110. These walls 500, 502 can advantageously provide additional fortification to ensure that the needle holder 110 does not get pushed out as the needle is inserted.

The needle holder array 112 described above can facilitate the insertion of multiple needles. For example, multiple needles (up to 30) can be inserted at one time. The configuration of the grid can be arranged such that the spacing between an entry point of the needle lock device 108 is between 5 to 10 mm. This configuration enables translational and rotational freedom of needle placement. For example, rotational freedom of each needle can be up to 10-30 degrees and there is no restriction to the position of the needle tip. As such, the needle holders 110 can be angulated to the required position and locked in place.

Figure 6A:
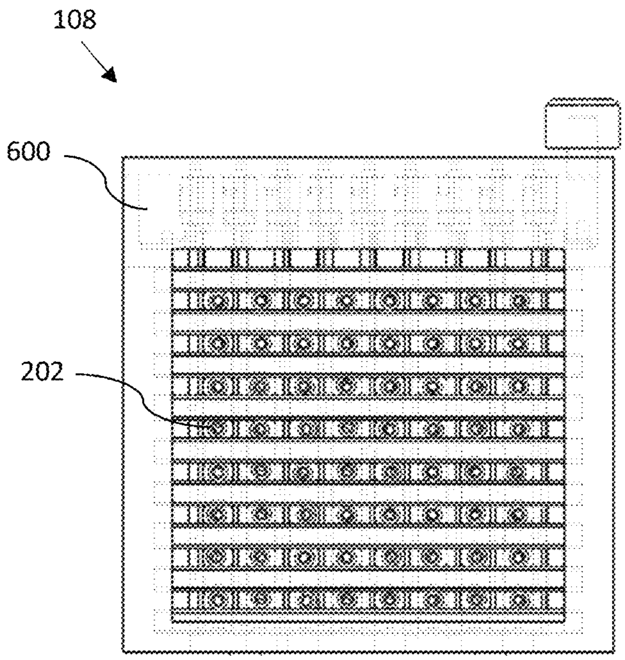
FIG. 6A shows a front view of a needle lock device with passages facing the front, according to an embodiment.
Figure 6B:
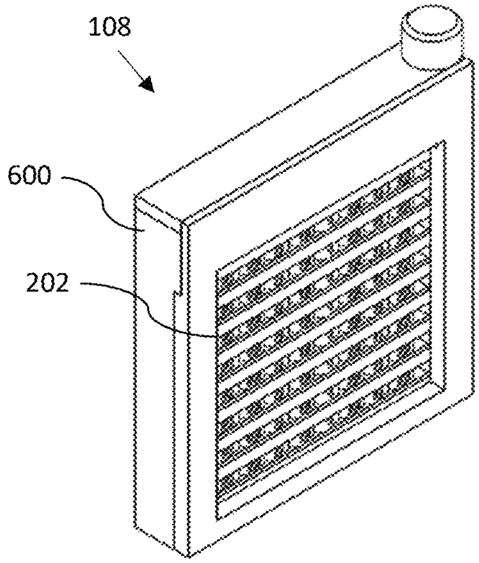
FIG. 6B shows perspective view of the needle lock device of FIG. 6A.
Figure 6C:
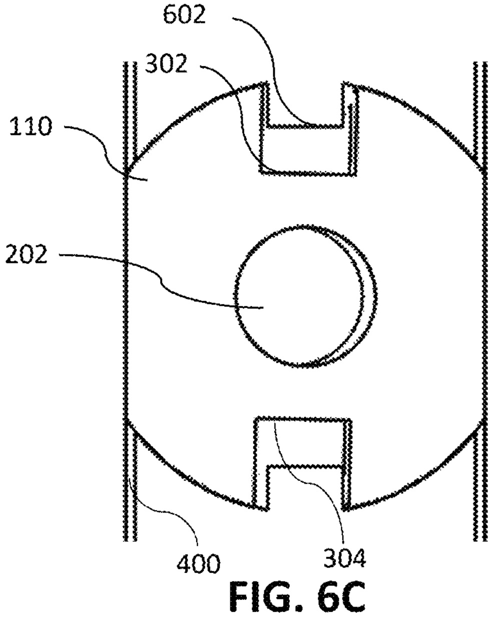
FIG. 6C shows a close-up front view of a needle holder being constrained by pins, according to an embodiment.
Figure 6D:
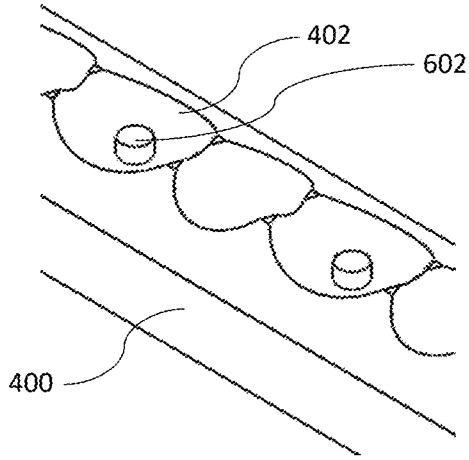
FIG. 6D shows a close-up view of a pin in each recess in a support member, according to an embodiment.

FIGS. 6A and 6B show a front view and a perspective view of the needle lock device 108 with the passages 202 facing the front. Typically, the passage 202 in the needle holders 110 should be facing the front to facilitate needle insertion by ensuring precise needle entry points. As such, the needle holders 110 should be facing the front directly, or at most rotate within limits so that the passage 202 is still accessible from the front. To do so, alignment members can be implemented to align a longitudinal axis of the passage 202 of a respective needle holder 110 along a direction substantially perpendicular to a plane formed by the outer frame 600. FIG. 6C illustrates a close-up front view of the needle holder 110 being constrained by a pin 602 such that the passage 202 is facing the front. As illustrated in FIG. 6D, the pin 602 can protrude from a respective recess 402 in the support member 400. For example, the pin 602 can sit within the slot 302 or 304 (FIG. 3) of the needle holder 110 such that the needle holder 110 when not in use is aligned to a direction where the passage 202 is substantially facing the front. Alternatively, the needle holders 110 can have ridges (not shown) that protrude from the holes of the walls 500, 502 at the front 504 and back 506. Alternatively, a fixture that slots into all the needle holders 110 can be used to keep the needle holders 110 in place. Such fixture can be removed right before a medical procedure.

In use, when the needles are at the respective desired positions, the needles should be locked securely in place such that their displacement is less than 3 mm in any direction. To achieve this, the lock mechanism 114 is implemented which is further described below.

In one embodiment, the support members 400 are arranged to be parallel to each other. In this embodiment, the lock mechanism 114 comprises a plurality of parallel lock members 700 (FIGS. 7A, 7B) mounted to the outer frame 600. The lock members 700 are substantially perpendicular to the support members 400. The support members 400 and lock members 700 define a grid for containing the needle holders 110. Each lock member 700 can have a cam profile and is configured to rotate between a first position and a second position to operate an adjacent needle holder 110 between a free state 702 (FIG. 7A) and a locked state 704 (FIG. 7B).

Figure 7A:
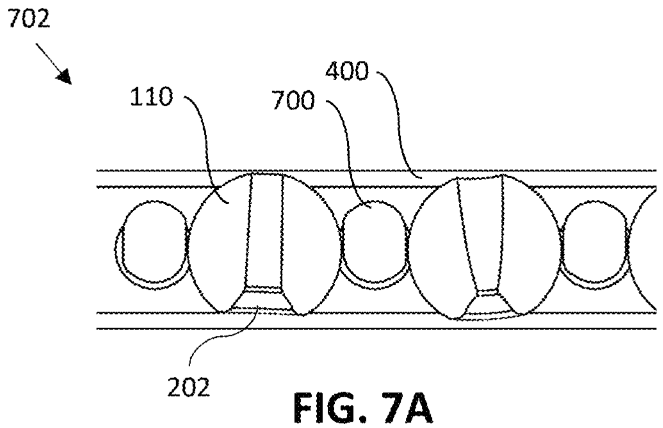
FIG. 7A shows a cross-section view of needle holders in a free state, according to an embodiment.
Figure 7B:
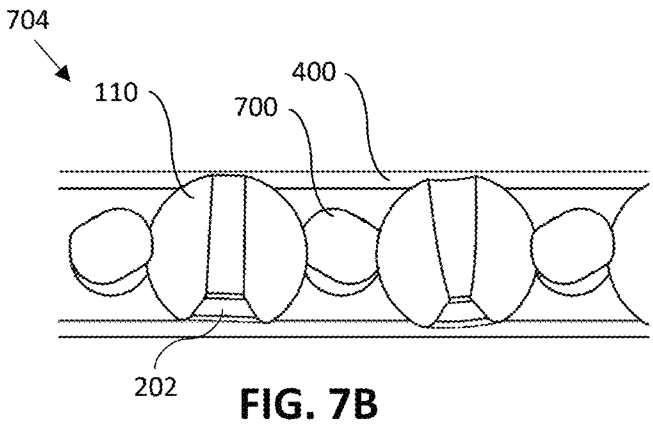
FIG. 7B shows a cross-section view of the needle holders of FIG. 7A in a locked state, according to an embodiment.

FIGS. 7A and 7B illustrate the needle holder 110 in the free state 702 and locked state 704. In the free state 702, the lock members 700 adjacent to each needle holder 110 is in the first position and do not exert any force on the needle holder 110. The needle holder 110 in this state is free to rotate or movable relative to the outer frame 600 and translation of a needle through the passage 202 is allowed. In the locked state 704, the lock members 700 are rotated to the second position. This results in compression of the needle holders 110, restricting their movement, and effectively causing them to clamp the needle such that translation of the needle through the passage 202 can be prevented. Further, in some implementations, prior to the insertion of needles, the lock members can apply appropriate compressive forces (i.e. pre-tensioning) to the needle holders 110 such that the passage 202 is generally facing the front when the needle holders 110 are in the free state.

Optionally, the lock members 700 on either side can rotate in opposite directions, such that the torque is balanced. This way, the needle holders 110 do not rotate sideways as the lock members 700 are rotated.

Locking action can be performed by turning a knob or lever. The torque is transmitted by a mechanism to lock the lock members 700. The lock members 700 can also be controlled either individually or collectively. For example, turning the knob or lever can move all lock members 700 between the first position and the second position. Such configuration can provide a simple construction of the needle lock device 108. In another example, at least two adjacent lock members 700 can be separately controlled by the knob or lever. Doing so can allow selective locking of a target column of needle holders 110 within the grid while providing rotational freedom of the other needle holders 110. This configuration can be useful in a medical procedure that requires insertion of multiple needles.

Alternative methods of locking the needle holders 110 are possible, for example, disposing wedges that are pulled upwards to compress the needle holders 110 against the support members 400. Additionally, the locking of the needle holders 110 based on the above embodiments can be enhanced by including rigid shells that confirm to the needle holders 110 on either side.

Figure 8A:
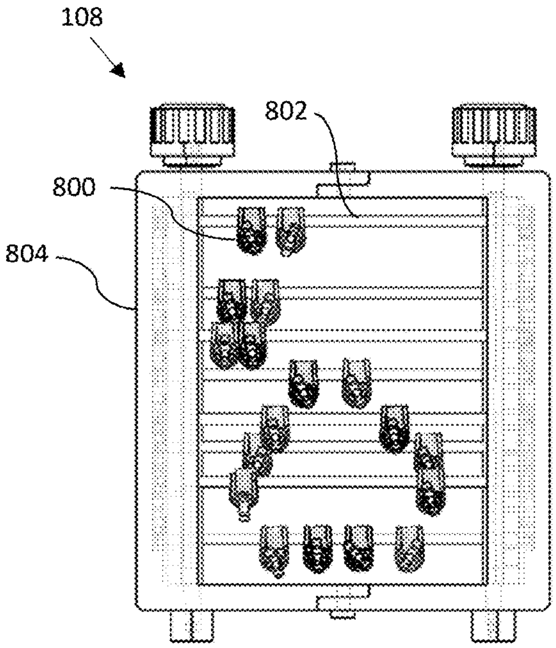
FIG. 8A shows a front view of a needle lock device, according to an alternate embodiment.
Figure 8B:
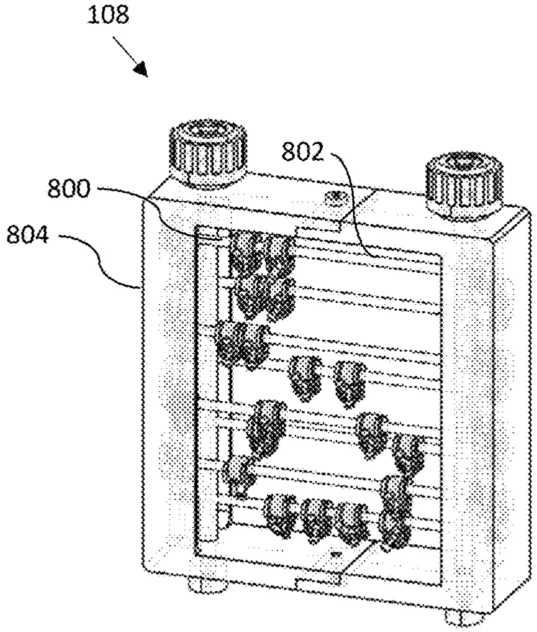
FIG. 8B shows perspective view of the needle lock device of FIG. 8A.
Figure 9A:
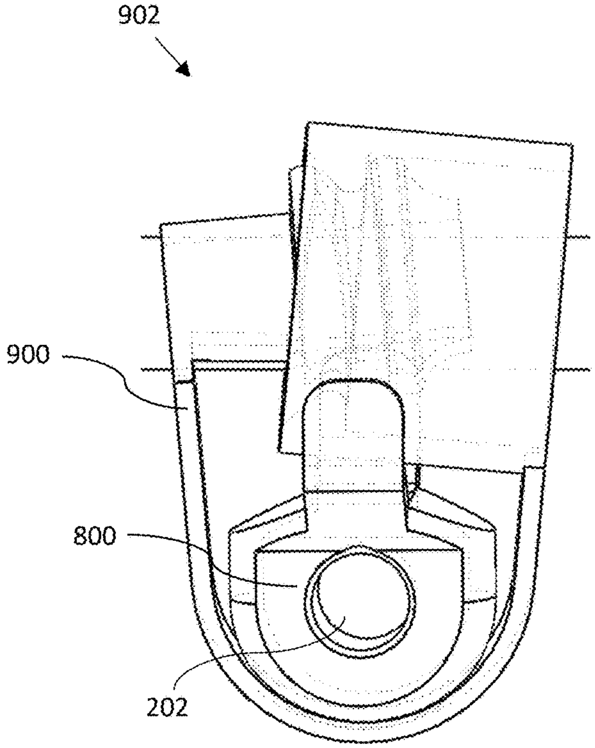
FIG. 9A shows a close-up view of a needle holder of the needle lock device of FIG. 8A in a free state, according to an embodiment.
Figure 9B:
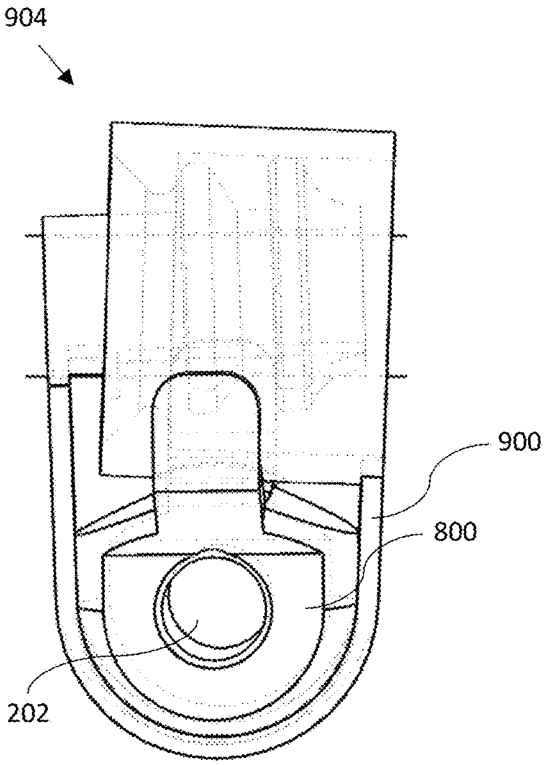
FIG. 9B shows a close-up view of the needle holder of FIG. 9A in a locked state, according to an embodiment.

In another embodiment, the needle holders 800 can be threaded on each of the support members 802 as illustrated in FIGS. 8A and 8B. Each of the support members 802 can be in the form of an elongated rod having ends supported by the outer frame 804 and being rotatable along its longitudinal axis. A series of support members 802 can be arranged in parallel to allow for spatial distribution of the needle holders 800 in the normal direction. The needle holders 800 are free to slide along the support member 802 and are swivelable about the respective support member 802 that the needle holders 800 are threaded onto. The support members 802 can be mounted on an offset axis (i.e. they are not all disposed on the same plane) to provide more freedom of positioning the needle. In this embodiment, the lock mechanism 114 comprises a plurality of clasps 900 (FIGS. 9A, 9B). Each clasp 900 can be attached to a respective needle holder 800. The clasps 900 are configured to operate the needle holder 800 between the free state 902 (FIG. 9A) and the locked state 904 (FIG. 9B).

FIGS. 9A and 9B illustrate the needle holder 800 in the free state 902 and locked state 904. In the free state 902, there is minimal compressive force on the needle holder 800 applied by clasp 900, and the needle holder 800 is free to rotate. In the locked state 904, the clasp 900 is pressed together, gripping the support member 802 and restricting horizontal movement along the support member 802. The gripping action also compresses the needle holder 800 in place, restricting its rotation, effectively causing it to clamp the needle. Further, the lock mechanism 114 can also lock the support members 802 (such as by clamping the support members 802 to the outer frame 804, either one at a time or all at once) to ensure they no longer rotate. This prevents vertical movement of the needle holders 800.

It will be appreciated by the person skilled in the art that the locking of the needle holders 110, 800 or support members 802 is not limited to the above embodiments but may, for example, also encompass locking through hydraulic or pneumatic means without departing from the scope of the present disclosure.

Additionally, the needle lock device 108 can have two cylindrical rods protruding at the bottom, which fit into corresponding holes in the ultrasound probe stepper system to assist with mounting the needle lock device 108. Therefore, the physical supporting structure 116 for the needle lock device 108 is compatible with commercially available third-party ultrasound probe stepper systems, or robotic navigation systems which allow flexible placement of needles.

Figure 10:
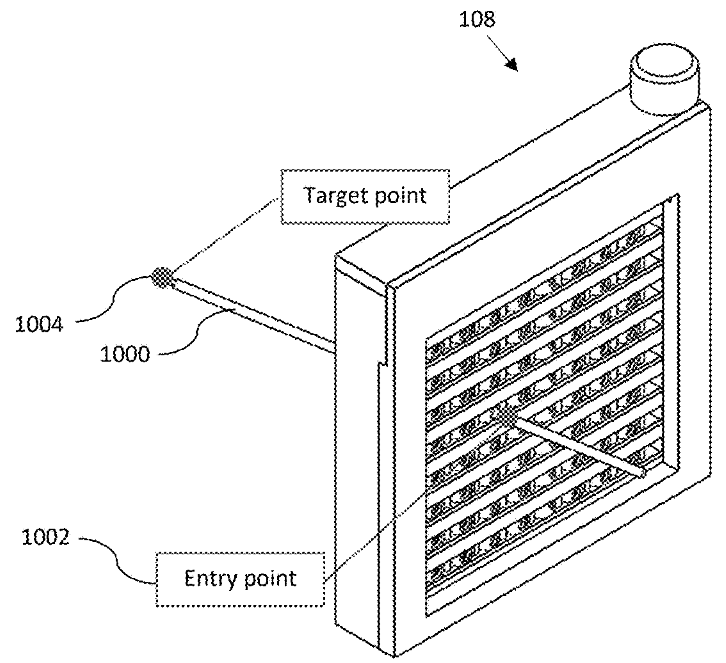
FIG. 10 shows perspective view of a needle guide system guiding a needle to through entry point based to a target point, according to an embodiment.

Advantageously, the needle lock device 108 can be used with a needle guide system 118 so that needles can be easily inserted through points of entry compatible with those on the needle lock device 108. FIG. 10 illustrates how the needle guide system 118 guides a needle 1000 to an entry point 1002 defined by the needle lock device 108 in a direction such that the needle 1002 can strike a desired target point 1004.

Figure 11:
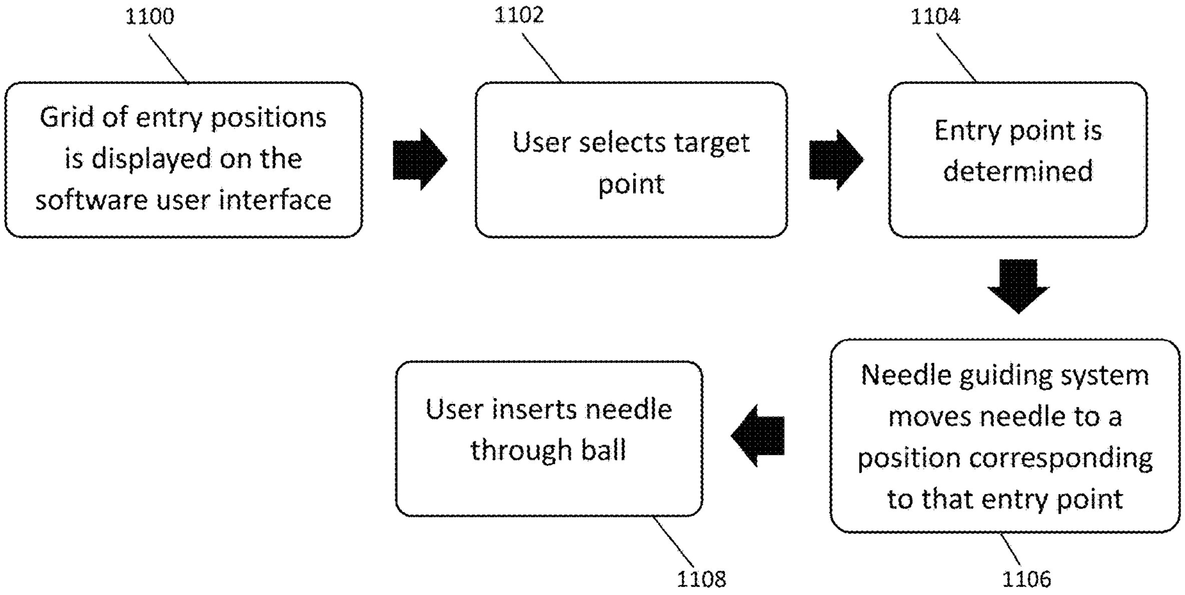
FIG. 11 shows a flowchart illustrating a workflow of a needle guide system, according to an embodiment.

With reference to FIG. 11, an example workflow of the needle guide system 118 comprises the following steps. In a first step 1100, a virtual grid is displayed on the software user interface to provide a reference for users. In a second step 1102, the user may select a target point 1004 on a region of interest. In a third step 1104, the entry point 1002 is determined by the system. In a fourth step 1106, the needle guide system 118 moves the needle 1000 to a position corresponding to the determined entry point 1002. In a fifth step 1108, the user inserts the needle 1000 through the needle holder 110, 800. The software plan for needle placement is geometrically aligned to ensure needles 1000 enter through the needle holders 110, 800. The software provides users the option to angulate needles 1000, such that there is no restriction to the position of the target point 1004. Advantageously, the needle guide system 118 can be applicable to all treatment modalities.

Figure 12:
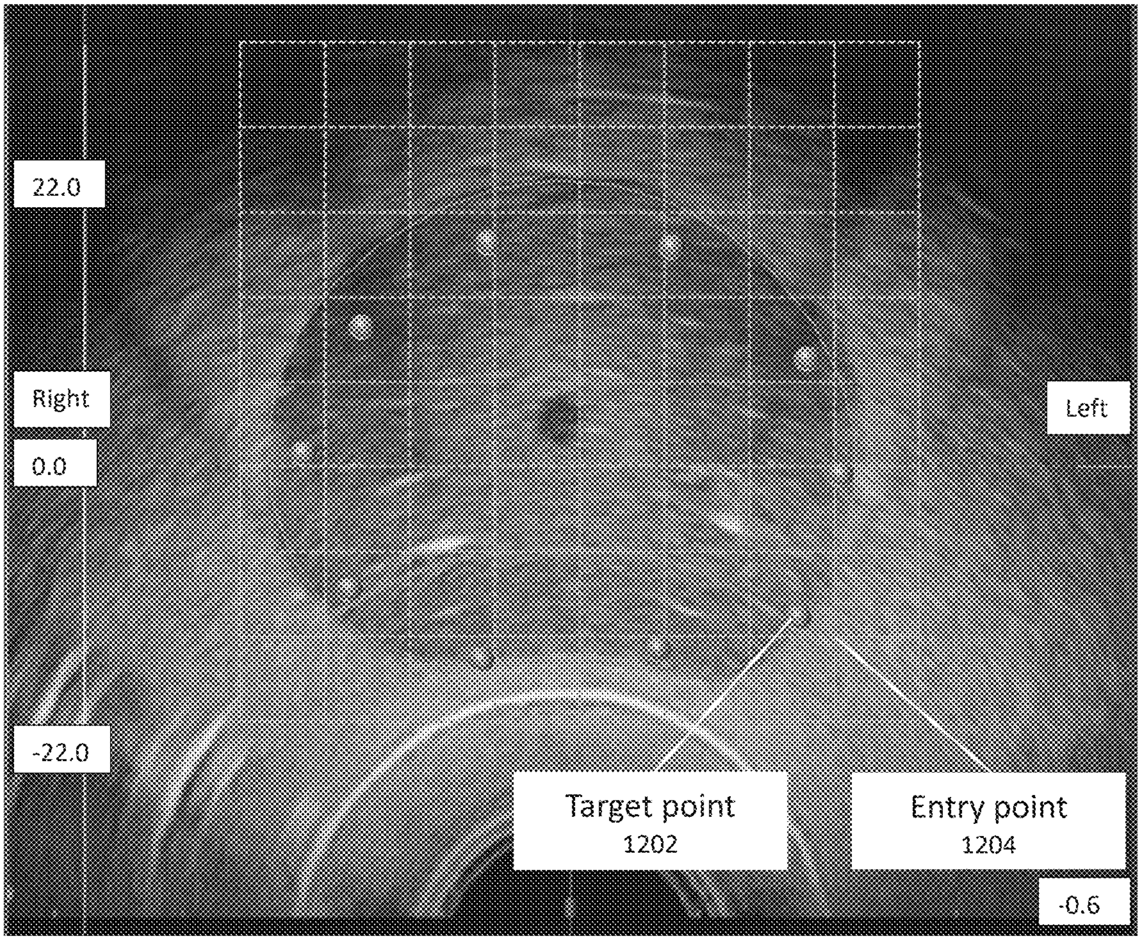
FIG. 12 shows an ultrasound scan image with a virtual grid displayed on the image, according to an embodiment.
Figure 13:
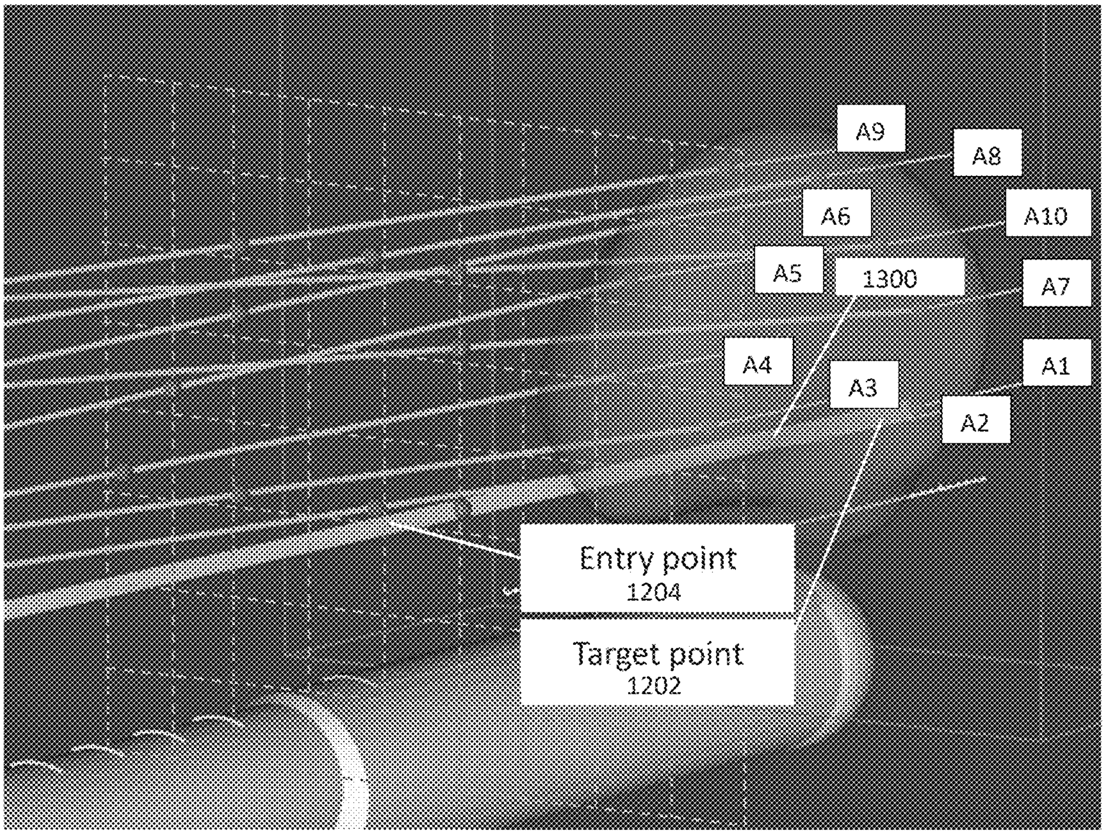
FIG. 13 shows a visualisation of needle trajectories passing through an entry point and a target, according to an embodiment.

FIG. 12 provides an example implementation in which the needle guide system displays a plurality of all possible entry points on the user interface 1200. The user can select a target point 1202 on the user interface 1200, corresponding to a position that will facilitate treatment of the region of interest. Based on the selected target point 1202, the needle guide system can determine the closest possible entry point 1204. Additional rules may apply to the needle guide system 118. For example, if another needle is present in the determined closest possible entry point 1204, then the next closest entry point will be used. If it is determined that the needle trajectory passes through critical structures such as the urethra, then another entry point can be selected to avoid such a scenario. Alternatively, the user can select or adjust the entry point 1204 for the needle 1000. As shown in FIG. 13, the needle trajectory 1300 can be displayed passing through these two points (i.e., entry point 1204 and target point 1202) to provide an indication to the user of which entry point 1204 will be used.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A needle lock device comprising:

an outer frame;

a plurality of support members mounted to the outer frame;

a plurality of needle holders, wherein at least one needle holder is disposed on each of the support members, each needle holder defining a passage configured to receive a needle; and a lock mechanism configured to operate each needle holder between a free state and a locked state, wherein, in the free state, the needle holder is movable relative to the outer frame and allows translation of the needle through the passage, and wherein, in the locked state, the needle holder is fixed relative to the outer frame and prevents translation of the needle through the passage, wherein each of the support members comprises an elongated rod having ends supported by the outer frame, the elongated rod being rotatable about its longitudinal axis.

2. The device of claim 1, wherein each needle holder is compressible for varying a size of the passage between the free state and the locked non state.

3. The device of claim 2, wherein each needle holder comprises at least one slot configured to reduce a force for compressing the needle holder.

4. The device of claim 1, wherein each support member comprises at least one concave recess, and wherein each of the at least one needle holder is disposed in a respective concave recess.

5. The device of claim 4, further comprising an alignment members protruding from each respective concave recess to align a longitudinal axis of the passage of a respective needle holder along a direction substantially perpendicular to a plane formed by the outer frame.

6. The device of claim 4, further comprising a protrusion configured to retain each needle holder in the respective concave recess.

7. The device of claim 4, wherein the plurality of support members are parallel to each other, and wherein the lock mechanism comprises a plurality of parallel lock members mounted to the outer frame such that the support members are substantially perpendicular to the lock members, the support members and lock members defining a grid for containing the needle holders.

8. The device of claim 7, wherein each lock member comprises a cam profile and is rotatable between a first position and a second position for operating an adjacent needle holder between the free state and the locked state.

9. The device of claim 8, wherein each lock member is configured to rotate at an opposite direction from an adjacent lock member.

10. The device of claim 1, wherein the at least one needle holder is slidable and swivelable about the respective support member.

11. The device of claim 10, wherein the lock mechanism comprises a plurality of clasps, wherein each clasp is attached to a respective needle holder and configured to operate the needle holder between the free state and the locked state.

12. The device of claim 1, wherein the lock mechanism is further configured to restrict rotation of selected one or more support members.

13. A needle guide system comprising:

the needle lock device according to claim 1;

a user interface device; and a processor;

wherein the user interface device is configured to provide a plurality of entry points corresponding to the passages of the plurality of needle holders; and wherein, based on a selected target point, the processor is configured to determine an entry point satisfying one or more parameters.

14. The needle guide system of claim 13, wherein the one or more parameters comprise a shortest distance between the entry point and the target point.

15. The needle guide system of claim 13, wherein the one or more parameters comprise an absence of a critical structure between the entry point and the target point.

16. The needle guide system of claim 13, wherein the one or more parameters comprise a preset angle between the entry point and the target point.

* * * * *